US005723106A

United States Patent [19]
Buch et al.

[11] Patent Number: 5,723,106
[45] Date of Patent: Mar. 3, 1998

[54] REDUCED ALCOHOL MOUTHWASH ANTISEPTIC AND ANTISEPTIC PREPARATION

[75] Inventors: R. Michael Buch, Hackettstown; Thomas A. Biemer, Great Meadows; Frank A. Volpe, Kinnelon, all of N.J.

[73] Assignee: Warner-Lambert Company, Morris Plains, N.J.

[21] Appl. No.: 784,609

[22] Filed: Jan. 21, 1997

Related U.S. Application Data

[63] Continuation of Ser. No. 318,008, Oct. 4, 1994, abandoned, which is a continuation of Ser. No. 9,617, Jan. 27, 1993, abandoned.

[51] Int. Cl.$^6$ ................................ A61K 7/16; A61K 7/26
[52] U.S. Cl. ..................................... 424/49; 424/58
[58] Field of Search ............................... 424/49–58

[56] References Cited

U.S. PATENT DOCUMENTS

| | | | |
|---|---|---|---|
| 2,435,744 | 2/1948 | Hartman | 99/140 |
| 2,508,978 | 5/1950 | Tribble | 99/140 |
| 3,164,524 | 1/1965 | Fand et al. | 167/93 |
| 3,674,502 | 7/1972 | Haney et al. | 99/28 |
| 3,864,472 | 2/1975 | Pensak et al. | 424/54 |
| 3,947,570 | 3/1976 | Pensak et al. | 424/54 |
| 4,130,638 | 12/1978 | Dhabhar et al. | |
| 4,150,151 | 4/1979 | Pader et al. | 424/56 |
| 4,465,661 | 8/1984 | Schmolka | 424/49 |
| 4,476,107 | 10/1984 | Schmalka | 424/49 |
| 4,479,673 | 10/1984 | Inaba et al. | |
| 4,550,018 | 10/1985 | Ambike et al. | 424/52 |
| 4,645,663 | 2/1987 | Grollier et al. | |
| 4,666,708 | 5/1987 | Goldemburg et al. | 424/49 |
| 4,684,517 | 8/1987 | Clipper et al. | 424/52 |
| 4,894,220 | 1/1990 | Nabi et al. | 424/52 |
| 4,923,685 | 5/1990 | Wullkniti et al. | 424/54 |
| 4,945,087 | 7/1990 | Talwar et al. | 514/60 |
| 4,992,259 | 2/1991 | Schiraldi et al. | 424/49 |
| 4,992,276 | 2/1991 | Dills et al. | 424/239 |
| 5,015,464 | 5/1991 | Struebridge | 424/48 |
| 5,100,650 | 3/1992 | Carun et al. | 424/52 |
| 5,256,401 | 10/1993 | Duckenfield et al. | 424/49 |
| 5,298,238 | 3/1994 | Hussein et al. | 424/49 |
| 5,405,604 | 4/1995 | Hall | 424/54 |

FOREIGN PATENT DOCUMENTS

| | | |
|---|---|---|
| 244363 | 11/1987 | European Pat. Off. |
| 277400 | 8/1988 | European Pat. Off. |
| 338978 | 10/1989 | European Pat. Off. |
| 497476 | 5/1992 | European Pat. Off. |
| 2106394 | 5/1972 | France . |
| 1361633 | 7/1974 | United Kingdom . |

OTHER PUBLICATIONS

Janistyn, Handbuch der Kosmetika und Riechstoffe, band 3. Die Körperpflegemittel 1973, Hüthig, DE see p. 788, example "Mundwasser amerikanische Type".

Advertising Age Mar. 16, 1992 Cool Mint Listerine has Lower Alcohol Content than Original Listerine.

Advertising Age Sep. 25, 1991 p. 70 Listerine 26.9% Alcohol has A.D.A. Seal of Approval It's No. 1 Mouthwash 30% of $8,000,000 U.S. Market.

Advertising Age Apr. 29, 1991 p. 50 ADA Looks at Listerine—26.9% Alcohol.

Federal Register 58 Fr. 54466 vol. 58 No. 202 oct. 21, 1993 Over the Counter Drug Products Intended for Oral Ingestion that Contain Alcohol—Dec. 17, 1992 Meeting of OTC Drugs Advisory Committee.

Federal Register 59 FR 6084 vol. 59 No. 127 Feb. 9, 1994 Oral Healthcare Drug Products for Over–the–Counter Human Use; Tentative Final Monograph for Oral and Septic Products—Dec. 17, 1992 OTC Drugs Advisory Comittee Recommended not More than the Minimum Amount of Alcohol Needed as a Solvent . . . etc.

Federal Register 59 FR 24386 vol. 59 No. 090 May 11, 1994 Proposed Rule: Mouthwash Packages Containing 3 Grams or More of Ethanol.

*Primary Examiner*—Shep K. Rose
*Attorney, Agent, or Firm*—Jean B. Barish; Evan J. Federman

[57] ABSTRACT

Reduced alcohol antiseptic mouthwash compositions are achieved which have the same oral antimicrobial efficacy, clarity and taste as higher alcohol level compositions. Availability of the active ingredients is best maintained by increasing the levels of surfactant employed in the composition together with the addition of two co-solvents, propylene glycol and glycerin. Propylene glycol with artificial sweetener(s), or propylene glycol alone with corresponding increases in the levels of surfactant are only marginally acceptable.

14 Claims, No Drawings

REDUCED ALCOHOL MOUTHWASH ANTISEPTIC AND ANTISEPTIC PREPARATION

This is a continuation application of U.S. Ser. No. 08/318,008 now abandoned, which is a continuation of prior application Ser. No. 08/009,617 filed on Jan. 27, 1993 now abandoned.

FIELD OF THE INVENTION

This invention is directed to reduced alcohol antiseptic and mouthwash compositions in which the clarity, taste and efficacy of the antiseptic mouth rinse is comparable to higher alcohol level formulations.

BACKGROUND OF THE INVENTION

Thymol is a well known compound which is utilized for its antimicrobial activity in a variety of preparations. In particular, thymol can be utilized in oral hygiene preparations such as mouth rinses in sufficient quantities to provide desired beneficial therapeutic effects. Listerine® is a well known antiseptic mouth rinse that has been used by millions for over one hundred years and has been proven effective in killing bacteria in the oral cavity that are responsible for plaque, gingivitis and bad breath. Thymol, methyl salicylate, menthol and eucalyptol are active ingredients in antiseptic mouth rinses such as Listerine® and achieve their efficacy although present in very minute amounts. Without being restricted to any specific theory, it is, now believed that efficacy and taste of antiseptic mouth rinses such as Listerine® is due to the availability or dissolution of these four active ingredients. Dissolution is also important from an aesthetic point of view in that a clear amber-colored mouthwash solution is certainly preferred by consumers to one that is cloudy or turbid or heterogeneous.

U.S. Pat. No. 4,945,087 to Talwar et al. discloses an oral antiseptic composition containing thymol, eucalyptol, menthol and methyl salicylate wherein the unpleasant, medicinal taste of thymol is masked using effective amounts of a sugar alcohol or a mixture of sugar alcohols and anethole. The ethanol level claimed is 5–35% and a level of 21.6% is disclosed.

U.S. Pat. No. 4,992,259 to Schiraldi et al. discloses a mouth rinse/dentifrice composition comprising a zinc salt co-dissolved with a naturally derived anionic polymer together with thymol, methyl salicylate and menthol in 13.5% ethanol. The mouth rinse is taught to be useful in the control and prevention of bad breath and calculus.

U.S. Pat. No. 4,479,673 to Iioka et al. and U.S. Pat. No. 4,645,663 to Nakashima et al. disclose oral compositions which contain menthol and methyl salicylate or eucalyptus oil which provides cleansing efficacy for teeth that are hypersensitive. The other actives are not disclosed however.

Finally, U.S. Pat. No. 4,130,638 to Dhabhar et al. discloses a sodium ricinoleate mouthwash composition comprising 10–25% ethanol, 0.5–2.5% of a Pluronic® surfactant together with thymol, menthol and eucalyptol. Methyl salicylate is not present and therefore not all four of the active ingredients are present.

It is therefore an object of the present invention to provide an antiseptic mouthwash formulation that is both efficacious in terms of killing the organisms responsible for plaque, periodontal disease and bad breath while at the same time providing such efficacy using reduced levels of alcohol and maintaining the characteristic organoleptic properties of Listerine® and other similar antiseptic-type mouth rinses. The efficacy, taste retention and clarity attributes are achieved at reduced alcohol levels of approximately 21.0% v/v by employing the surfactant levels from above 0.10% to less than 0.6% w/v. While it was believed that the non-ionic surfactant entraps a portion of the active ingredients and as such the suppressed dissolution/availability of actives would result in a reduction of efficacy as well as diminish the strong phenolic bite of the mouthwash, it was surprisingly and unexpectedly found that the addition of two co-solvents, propylene glycol and glycerin, in amounts whose combined percentage is less than the percent decrease in alcohol, enable the production of a reduced alcohol antiseptic mouthwash composition with levels of antiseptic efficacy and clarity, and desired organoleptic properties comparable to those of Listerine®.

DETAILED DESCRIPTION OF THE INVENTION

A reduced alcohol antiseptic mouthwash composition with optimal clarity and efficacy characteristics is achieved using four known active ingredients together with specific levels of surfactant and the serendipitous addition of two co-solvents, propylene glycol and glycerin.

The compositions of this invention include effective amounts of thymol and other active oils such as those selected from the group consisting of eucalyptol, menthol, methyl salicylate, and the like, and mixtures thereof. Generally, the total amount of actives present in a composition can be from about 0.05 to about 0.35% by weight, based on the weight of the composition, with about 0.16 to about 0.28% by weight of total volume of liquid oral preparation (% w/v) being preferred. For example, the compositions, as stated above, can contain eucalyptol, menthol, methyl salicylate, and thymol. Preferably the eucalyptol is present in amounts of about 0.07 to about 0.11% w/v being preferred and most preferably, from about 0.08 to about 0.10%. Menthol is preferably present in amounts of from about 0.02 to about 0.06% w/v by weight and most preferably from about 0.03 to about 0.05% w/v. Preferably, methyl salicylate is present in amounts of about 0.03 to about 0.08% by weight and most preferably from about 0.04 to about 0.07%. Finally, with respect to the actives, thymol is present in amounts of about 0.03 to about 0.09% by weight and most preferably from about 0.04 to about 0.07%, said % by weight being based on the total composition. In addition to these actives, benzoic acid is preferably present in amounts of about 0.1 to about 0.3% by weight, based on the total composition and most preferably from about 0.13 to about 0.18%.

Compositions or final products containing these active ingredients include liquid oral preparations such as a mouthwash spray or rinse. In such preparations, the vehicle, i.e. the carrier for the ingredients of the mouthwash, such as the actives, and the like, is typically a water-alcohol mixture. Generally the ratio of water to alcohol is in the range of from about 3:1 to about 25:1, preferably about 3.2:1 to about 20:1 and most preferably, about 3.5:1 to about 10:1 by volume. The total amount of water-alcohol mixture in a mouthwash preparation is typically in the range from about 80% to about 99.9% by volume of the total composition.

The co-solvents which are added to effectively aid in the dissolution of the active ingredients can be present in amounts to about 8.0% v/v each, the total amount of the solvents not to exceed about 16% v/v. Preferably, the propylene glycol will be present in an amount of from about 1.0 to about 4.0% v/v while the glycerin will be in an amount of from about 0.2 to about 3.0% v/v or will exist in ratios of from about 20:1 to about 1:3, propylene glycol/glycerin, respectively.

Sole additions of propylene glycol in quantities over 6.0% v/v add bitterness to the product which is offset by lesser quantities of sweeteners such as glycerin, sugar alcohols like sorbitol or artificial sweeteners like aspartame, saccharin or acesulfame. Sole additions of glycerin in amounts over 3.0% v/v add unwanted sweetness to the taste. Sole addition of propylene glycol without glycerin at 6.0% v/v or less and sole additions of glycerin at 3.0% v/v or less are not optimized and do not exhibit the same efficacious and organoleptic results but are marginally acceptable.

The pH value of such mouthwash preparations is generally from about 3.5 to about 8.0 and preferably from about 4.0 to about 7.5. A pH below 3.5 would be irritating to the oral cavity and dissolve tooth enamel. A pH greater than 8.0 would result in an unpleasant mouth feel.

Oral liquid preparations may also contain surface active agents, i.e. surfactants, in amounts up to about 5.0% and fluoride-providing compounds in amounts up to about 2.0% by weight of the preparation.

Surface active agents (surfactants) are organic materials which aid in the complete dispersion of the preparation throughout the oral cavity. The organic surface active material may be anionic, non-ionic, amphoteric, or cationic. Suitable anionic surfactants are water-soluble salts of higher fatty acid monoglyceride monosulfates, such as the sodium salt of the monosulfated monoglycerides of hydrogenated coconut oil fatty acids; higher alkyl sulfates, such as sodium lauryl sulfate; sodium alkylether sulfates such as sodium laurylether (1–4) sulfate, alkyl aryl sulfonates, such as sodium dodecyl benzene sulfonate; higher alkyl sulfoacetates; alkyl and alkylether phosphates such as sodium laurylether (4) phosphate; higher fatty acid esters of 1,2-dihydroxy propane sulfonates; ether sulfates; alkyl phosphates; and substantially saturated higher aliphatic acyl amides of lower aliphatic amino carboxylic acids such as those having 12 to 16 carbons at the fatty acid; alkyl or acyl radicals. Examples of the last mentioned amides are N-lauroyl sarcosine, and the sodium, potassium, and ethanolamine salts of N-lauroyl, N-myristoyl or N-palmitoyl sarcosine.

The non-ionic surfactants employed are poly (oxyethylene)-poly(oxypropylene) block copolymers. Such copolymers are known commercially as poloxamers and are produced in a wide range of structures and molecular weights with varying contents of ethylene oxide and propylene oxide. The non-ionic poloxamers according to the invention are non-toxic and acceptable as direct food additives. They are stable and readily dispersible in aqueous systems and are compatible with a wide variety of formulating ingredients for oral preparations. These surfactants should have an HLB (Hydrophilic-Lipophilic Balance) of between about 10 and 30 and preferably between 10 and 25.

Thus, non-ionic surfactants useful in this invention include poloxamers:

| 105 | 188 | 237 | 334 |
| 108 | 215 | 238 | 335 |
| 124 | 217 | 284 | 338 |
| 184 | 234 | 288 | 407 |
| 185 | 235 | 333 |     |

Generally these polymers should constitute from about 0.04% w/v to about 6.0% w/v by weight of total volume of liquid oral preparation (% w/v) and preferably from 0.11% to 0.17% w/v. A particularly preferred poloxamer is Poloxamer 407 having an HLB of about 22. Such a polymer is sold under the trademark Pluronic F-127® (BASF-WYANDOTTE).

Another class of non-ionic surfactants useful in this invention are ethoxylated hydrogenated castor oils. Such surfactants are prepared by hydrogenating castor oil and treating the so-formed product with from about 10 to 200 moles of ethylene glycol. They are designated as PEG (numeral) hydrogenated castor oil in accordance with the dictionary of the Cosmetics, Toiletries and Fragrance Association, 4th Ed. wherein the numeral following PEG indicates the degree of ethoxylation, i.e. the number of moles of ethylene oxide added. Suitable PEG hydrogenated castor oils include PEG 16, 20, 25, 30, 40, 50, 60, 80, 100 and 200. The ethoxylated hydrogenated castor oils are used in the same concentrations as the above described poly (oxyethylene)-poly(oxypropylene) block copolymers.

Other non-ionic surface active agents which may be suitable include condensates of sorbitan esters of fatty acids with from 20 to 60 moles of ethylene oxide (e.g., "Tweens"® a trademark of ICI United States, Inc.). Amphoteric agents such as quaternized imidazole derivatives and mixtures thereof may also be suitable.

Additional non-ionic surfactants which may be suitable are the condensation products of an alpha-olefin oxide containing 10 to 20 carbon atoms, a polyhydric alcohol containing 2 to 10 carbons and 2 to 6 hydroxyl groups and either ethylene oxide or a mixture of ethylene oxide and propylene oxide. The resultant surfactants are polymers having a molecular weight in the range of 400 to about 1600 and containing 40% to 80% by weight of ethylene oxide, with an alpha-olefin oxide to polyhydric alcohol mole ratio in the range of about 1:1 to 1:3.

Cationic surface active agents which may be suitable are molecules that carry a positive charge such as cetylpyridinium chloride.

Fluoride providing compounds may be present in the oral preparations of this invention. These compounds may be slightly water soluble or may be fully water soluble and are characterized by their ability to release fluoride ions or fluoride containing ions in water. Typical fluoride providing compounds are inorganic fluoride salts such as soluble alkali metal, alkaline earth metal, and heavy metal salts, for example, sodium fluoride, potassium fluoride, ammonium fluoride, cupric fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Tin fluoride, alkaline metal fluorides and monofluorophosphates such as sodium and stannous fluoride, sodium monofluorophosphate and mixtures thereof are preferred.

In an oral liquid preparation such-as a mouthwash, the fluoride providing compound is generally present in an amount sufficient to release up to about 0.15%, preferably about 0.001% to about 0.1% and most preferably from about 0.001% to about 0.05% fluoride by weight of the preparation.

In general, the compositions of this invention are prepared utilizing techniques well known to those skilled in the art. Thus, the liquid compositions may be prepared by mixing the alcohol soluble ingredients with ethanol, adding a quantity of water to the mixture thus obtained, and then blending or mixing in the water soluble ingredients. For example, in preparing one liter of a typical liquid oral composition, thymol, eucalyptol, menthol, methyl salicylate, surfactant and benzoic acid are dissolved in and mixed with ethanol. The co-solvents, propylene glycol and glycerin are added in ratios of from about 20:1 to about 1:3, respectively and to this resulting mixture a sufficient quantity of water is added to make up one liter.

Those skilled in the art will appreciate that the total amount of all ingredients (components) used in the compositions of this invention equals 100% by weight of the total composition. Also, unless stated otherwise, all percents herein are percent by weight of the total composition.

The following examples are illustrative only and should not be construed as limiting the invention in any way. Those skilled in the art will appreciate that variations are possible which are within the spirit and scope of the appended claims.

EXAMPLE 1

Example 1 sets forth four embodiments of the claimed reduced alcohol antiseptic mouthwash of the present invention.

TABLE I

| Ingredient | Ingred. Quantity Per Liter of Final Solutions |
| --- | --- |
| FORMULATION A | |
| 1) Alcohol USP (95% Ethanol) | 227.3700 mls |
| 2) Eucalyptol | .9220 gms |
| 3) Thymol NF | .6390 gms |
| 4) Menthol USP | .4250 gms |
| 5) Acid Benzoic USP | 1.5000 gms |
| 6) Hydrochloric Acid (10% V/V) | |
| 7) Sodium Hydroxide, 10% W/V Solution | |
| 8) Methyl Salicylate NF | .6000 gms |
| 9) Caramel, Acid Proof | .2150 gms |
| 10) Poloxamer 407 | 1.5000 mls |
| 11) Glycerin USP Special | 20.0000 mls |
| 12) Propylene Glycol USP | 20.0000 mls |
| 13) Water Potable | QS to 1.0000 L |
| FORMULATION B | |
| 1) Alcohol USP (95% Ethanol) | 227.3700 mls |
| 2) Eucalyptol | .9220 gms |
| 3) Thymol NF | .6390 gms |
| 4) Menthol USP | .4250 gms |
| 5) Acid Benzoic USP | 1.5000 gms |
| 6) Hydrochloric Acid (10% V/V) | |
| 7) Sodium Hydroxide, 10% W/V Solution | |
| 8) Methyl Salicylate NF | .6000 gms |
| 9) Caramel, Acid Proof | .2150 gms |
| 10) Poloxamer 407 | 1.5000 gms |
| 11) Glycerin USP Special | 5.0000 mls |
| 12) Propylene Glycol USP | 15.0000 mls |
| 13) Water Potable | QS to 1.0000 L |
| FORMULATION C | |
| 1) Alcohol USP (95% Ethanol) | 227.3700 mls |
| 2) Eucalyptol | .9220 gms |
| 3) Thymol NF | .6390 gms |
| 4) Menthol USP | .4250 gms |
| 5) Acid Benzoic USP | 1.5000 gms |
| 6) Hydrochloric Acid (10% V/V) | |
| 7) Sodium Hydroxide, 10% W/V Solution | |
| 8) Methyl Salicylate NF | .6000 gms |
| 9) Caramel, Acid Proof | .2150 gms |
| 10) Poloxamer 407 | 1.4000 gms |

TABLE I-continued

| Ingredient | Ingred. Quantity Per Liter of Final Solutions |
| --- | --- |
| 11) Glycerin USP Special | 5.0000 mls |
| 12) Propylene Glycol USP | 25.0000 mls |
| 13) Water Potable | QS to 1.0000 L |
| FORMULATION D | |
| 1) Alcohol USP (95% Ethanol) | 227.3700 mls |
| 2) Eucalyptol | .9220 gms |
| 3) Thymol NF | .6390 gms |
| 4) Menthol USP | .4250 gms |
| 5) Acid Benzoic USP | 1.5000 gms |
| 6) Hydrochloric Acid (10% V/V) | |
| 7) Sodium Hydroxide, 10% W/V Solution | |
| 8) Methyl Salicylate NF | .6000 gms |
| 9) Caramel, Acid Proof | .2150 gms |
| 10) Poloxamer 407 | 1.5000 gms |
| 11) Propylene Glycol USP | 50.0000 mls |
| 12) Water Potable | QS to 1.0000 L |

The alcohol, eucalyptol, thymol, menthol, benzoic acid, methyl salicylate, poloxamer, glycerin and propylene glycol are added together and mixed until complete dissolution is achieved. Water is then added in a sufficient quantity so that the volume is brought to 950 mls. Hydrochloric acid or sodium hydroxide is added to adjust the pH of the solution to between about 4.1–4.3. Both caramel and additional water are then added to add amber color and bring entire solution to a one (1) liter volume.

All examples exhibited significantly less turbidity or cloudiness at lower temperatures than standard commercially available antiseptic mouthwash. Sensory evaluation tests involving an expert taste panel also indicated none of the subjects disclosed any significant difference in the bitter, phenolic taste between these lower alcohol formulations and the standard commercially available product. Formulation D was only marginally acceptable.

EXAMPLE II

Reduced Alcohol Listerine Cosolvent Turbidity Studies

A number of reduced alcohol Listerine samples were prepared for nephelometric analysis. The samples were prepared with a 0.07% w/v Pluronic F-127® (Poloxomer 407) level to ensure turbidity levels within the optimal detection range of the Hach Ratio Turbidimeter. The lower the turbidity number, the clearer the solution. Generally levels above 10 are not acceptable for commercial purposes. Each of the samples was prepared by pipeting 22.7 ml aliquots of a stock actives/benzoic acid/ethanol solution and 5.0 ml of a 1.4% w/v aqueous Pluronic F-127® stock solution into 100 ml graduated cylinders. Before each sample was brought to 100 ml with tap water, varying volumes of propylene glycol and glycerin were added to the samples. The samples were then analyzed with the turbidimeter. Additionally, a sample was prepared according to the −250 formula, Formulation C set forth in Example I, (with 0.14% w/v Pluronic) and analyzed similarly. The results are listed in the following table. All percentages in the table are v/v.

| FORMULATION | TURBIDITY (N.T.U.) |
|---|---|
| 0% propylene glycol, 0% glycerin | >200 (off scale) |
| 0% propylene glycol, 2% glycerin | 70 |
| 1% propylene glycol, 1% glycerin | 20 |
| 2% propylene glycol, 0% glycerin | 8.7 |
| 2% propylene glycol, 2% glycerin | 5.9 |
| 2.5% propylene glycol, 0.5% glycerin | 4.5 |
| Formulation C | <0.1 (off scale) |

These results indicate that the mixture of the two cosolvents reduced the level of turbidity to a greater extent than did either of the individual solvents.

EXAMPLE III

In vitro efficacy assessments using the plaque penetration assay model have been correlated to clinical investigations. Both Listerine® and Listerine Cool Mint® have been shown to be clinically effective and both products were granted the Council on Dental Therepeutics American Dental Association acceptance seal for demonstrating that each product helps prevent and reduce supragingival plaque accumulation and gingivitis when used in a conscientiously applied program of oral hygiene and regular professional care. In vitro plaque penetration is a stringent test of the ability of an antiseptic to penetrate a dental plaque-like organic matrix and kill oral micro-organisms. a thick biofilm of *Streptococcus mutans* ATCC strain 25175. The results are listed in the following table.

| FORMULATION | CRITICAL KILL TIME (minutes) |
|---|---|
| A | 3.5 |
| B | 3.0 |
| C | 3.4 |
| Listerine ® | 3.2 |
| Listerine Cool Mint ® | 3.5 |

The results indicate that each formulation of the two cosolvents provide comparable oral antimicrobial efficacy to higher alcohol level compositions.

What we claim is:

1. An organoleptically acceptable antiseptic mouthwash composition comprising an effective amount of thymol, eucalyptol, methyl salicylate and menthol dissolved in ethanol, said ethanol being present in an amount of no more than 22% v/v; a dispersion effective amount of surfactant; a co-solvent effective amount of a combination of propylene glycol and glycerin; benzoic acid; and water wherein the propylene glycol is present in an amount of from about 1.0% to about 4.0% v/v and said glycerin is present in an amount of from about 0.2% to about 3.0% v/v.

2. The antiseptic mouthwash composition of claim 1 wherein said surfactant is selected from the group consisting of anionic, non-ionic, amphoteric and cationic surface active agents.

3. The antiseptic mouthwash compositions of claim 2 wherein said non-ionic surfactants are selected from the group consisting of poloxamers.

4. The antiseptic mouthwash compositions of claim 3 wherein said poloxamer constitutes from 0.01–0.2 weight percent of the total mouthwash composition.

5. The antiseptic mouthwash composition of claim 4 wherein said glycerin and propylene glycol are present in amounts up to 6.0% volume of the total mouthwash composition.

6. The antiseptic mouthwash composition of claim 5 wherein said propylene glycol is present in said antiseptic mouthwash in an amount of from about 1.0% to about 4.0% v/v and said glycerin is present in an amount of from about 0.2 to about 3.0% v/v.

7. The antiseptic mouthwash composition of claim 5 wherein the ratio of propylene glycol to glycerin present in the compositions is from about 20/1 to about 1/3, respectively.

8. The antiseptic mouthwash of claim 7 wherein said poloxamer is Poloxamer 407.

9. The antiseptic mouthwash of claim 8 wherein said alcohol is ethanol.

10. The antiseptic mouthwash composition of claim 9 wherein said thymol is present in an amount of from about 0.04% to about 0.07% w/v.

11. The antiseptic mouthwash composition of claim 10 wherein said eucalyptol is present in an amount of from about 0.08% to about 0.10% w/v.

12. The antiseptic mouthwash of claim 11 wherein said menthol is present in an amount of from about 0.03% to about 0.05% w/v.

13. The antiseptic mouthwash of claim 12 wherein said methyl salicylate is present in amounts of from about 0.04% to about 0.07% w/v.

14. The antiseptic mouthwash of claim 1 wherein said propylene glycol is present in an amount of about 2.5% v/v and said glycerin is present in an amount of about 0.5% v/v.

* * * * *